United States Patent [19]

Frank

[11] 4,269,938
[45] May 26, 1981

[54] ASSAY OF PEROXIDATIVELY ACTIVE MATERIALS

[75] Inventor: David S. Frank, Rochester, N.Y.

[73] Assignee: Eastman Kodak Company, Rochester, N.Y.

[21] Appl. No.: 18,532

[22] Filed: Mar. 8, 1979

[51] Int. Cl.³ .................. G01N 31/14; C09K 3/00; G01N 31/22

[52] U.S. Cl. .................... 435/7; 23/230 B; 252/408; 252/186; 252/188.3 CL; 252/301.16; 422/55; 422/56; 422/57; 422/61; 424/7; 424/8; 424/12; 435/14; 435/28; 435/188

[58] Field of Search ........... 435/7, 14, 28, 188; 252/408, 186, 188.3 CL, 301.16; 424/7, 8, 12; 23/230 B; 422/61, 56, 57, 55

[56] References Cited

U.S. PATENT DOCUMENTS

| | | | |
|---|---|---|---|
| 3,654,090 | 4/1972 | Schuurs et al. | 435/188 |
| 3,791,932 | 2/1974 | Schuurs et al. | 435/188 |
| 3,850,752 | 11/1974 | Schuurs et al. | 435/188 |
| 3,964,870 | 6/1976 | Tiedemann | 435/28 |
| 3,992,158 | 11/1976 | Przybylowicz et al. | 435/28 |
| 4,042,335 | 8/1977 | Clement | 435/14 |
| 4,069,016 | 1/1978 | Wu | 23/230 B |
| 4,089,747 | 5/1978 | Bruschi | 435/28 |

FOREIGN PATENT DOCUMENTS 2811228 9/1978 Fed. Rep. of Germany .............. 435/7

OTHER PUBLICATIONS

Keston, A. et al., Anal. Biochem., vol. 11, pp. 1-5 (1965).
Brandt, R. et al., Anal. Biochem., vol. 11, pp. 6-9 (1965).
Black, M. J. et al., Anal. Biochem., vol. 58, pp. 246-254 (1974).

*Primary Examiner*—Teddy S. Gron
*Attorney, Agent, or Firm*—Arthur H. Rosenstein

[57] ABSTRACT

A new peroxidase assay for substances demonstrating peroxidative activity is described which is based on the peroxidase catalyzed oxidation of dichlorofluorescin to dichlorofluorescein by peroxide. The dichlorofluorescin is formed from diacetyldichlorofluorescin either by the direct addition of peroxide or by the inclusion of a peroxide generating system (e.g., glucose plus glucose oxidase or uric acid and uricase) in the reaction mixture. As long as all reactants other than the peroxidase are present in excess, the rate of fluorescence increase is linearly related to the amount of peroxidase in the sample under assay.

41 Claims, 1 Drawing Figure

ASSAY OF PEROXIDATIVELY ACTIVE MATERIALS

BACKGROUND OF THE INVENTION

1. Field of the Invention

The present invention relates to a rapid, sensitive assay for peroxidase. More particularly, the present invention relates to a composition, element and method for carrying out a simplified, fluorometric peroxidase assay useful for detecting low enzyme levels.

2. Description of the Prior Art

The oxidation of dichlorofluorescin by hydrogen peroxide to dichlorofluorescein, catalyzed by the enzyme peroxidase, has been used as an assay technique for hydrogen peroxide (Black, M. J. & Brandt, R. B., Anal. Biochem, 58:241 [1974]). A drawback of this technique is that since the dichlorofluorescin is unstable to air oxidation, it must be generated as needed by hydrolysis of diacetyldichlorofluorescin at alkaline pH followed by neutralization and dilution in the assay tube.

The assay of peroxidase, particularly at relatively low levels, is useful in certain immunoassay techniques wherein a peroxidase is used as the label for a ligand in a competitive binding or displacement immunological determination. Such assay techniques are described in U.S. Pat. No. 3,817,837 to Rubenstein et al; U.S. Pat. No. 3,154,090 to Schuurs et al and in Van Weeman, B. K. and Schuurs, A.H.W.M., BIOCHIMIE, 54:842 (1972).

Thus, there is a need for a peroxidase assay which is capable of detecting low levels of the enzyme, i.e., on the order of $\leq 10^{-7}$ M as are used in immunoassays. Such an assay desirably would be rapid and eliminate the requirement of the prior art fluorometric peroxidase assay system that the dichlorofluorescin be prepared as needed in a separate step. Furthermore, as with any similar assay technique, it is most desirable that all of the reagents can be stored in a stable, dry condition until immediately prior to use.

SUMMARY OF THE INVENTION

A new peroxidase assay for substances demonstrating peroxidative activity is described which comprises the steps of (1) contacting an assay composition comprising diacetyldichlorofluorescin and a source of hydrogen peroxide with a sample to be assayed and (2) detecting the resulting dichlorofluorescein which is formed from the peroxidase catalyzed oxidation of the reaction product of diacetyldichlorofluorescin with hydrogen peroxide. In a preferred embodiment, the dichlorofluorescein is detected by rate of fluorescence increase. As long as all reactants other than the peroxidase are present in excess, the rate of fluorescence increase is linearly related to the amount of peroxidase in the sample under assay.

The present invention also provides dry reagent compositions which include all of the materials required to perform peroxidase determination. Such composition can be stored dry and provide stable and adaptable compositions for a multitude of applications wherein peroxidase detection and/or quantification may be useful or desirable.

The assay compositions of the present invention comprise diacetyldichlorofluorescin, hydrogen peroxide or a composition which generates hydrogen peroxide (i.e., a source of hydrogen peroxide), e.g., glucose and glucose oxidase or uric acid and uricase, and generally a buffer to maintain the pH of the assay composition at between about 7 and 9.

A further embodiment of the present invention comprises an element for the detection of peroxidase comprising a spreading layer and a reagent layer in fluid contact under conditions of use, said reagent layer comprising diacetyldichlorofluorescin and a source of hydrogen peroxide.

In a still further embodiment of the present invention, a method of assaying for antigen or antibody present in a sample comprises:

(a) labeling a known amount of antigen or antibody with a peroxidase and adding said labeled antigen or antibody with said sample to be assayed to a known amount of corresponding antigen or antibody; and (b) detecting the amount of unknown antigen or antibody by (1) contacting in an aqueous medium the mixture of (a) and a composition comprising diacetyldichlorofluorescin and a source of hydrogen peroxide to produce dichlorofluorescein and (2) detecting the dichlorofluorescein.

Particular advantages of the peroxidase assay method described herein are:

(1) Simplicity: dichlorofluorescin is generated in situ during the assay reaction, thus eliminating costly preparation steps;

(2) Reagent Stability: since all required reagents are capable of dry storage, the assay composition exhibits extended shelf life and can be adapted to numerous assay applications;

(3) Speed: the assay compositions described herein are capable of assaying for peroxidase activity in one minute or less.

DETAILED DESCRIPTION OF THE INVENTION

Figure 1:
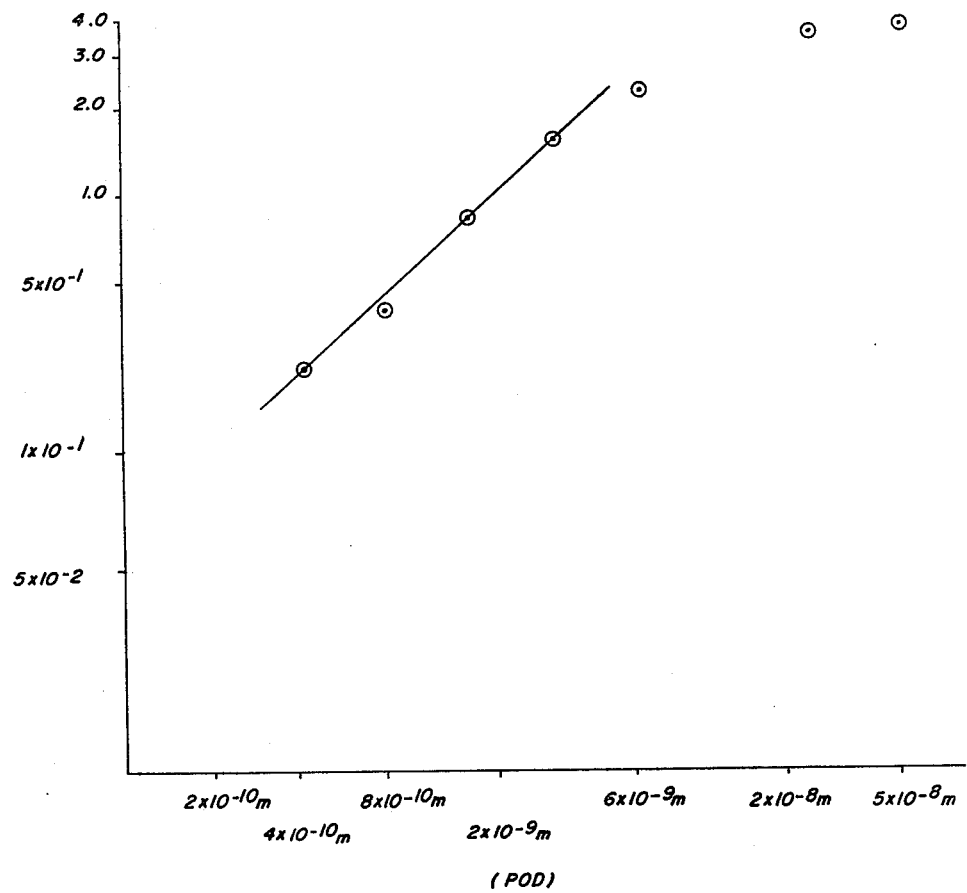
FIG. 1 shows a graph of fluorescent rate measurement against peroxidase concentration.

The term "peroxidase" as used herein is meant to include all those materials which are commonly known to possess "peroxidative activity." Peroxidative activity is well known in the art and includes, for example, peroxidative enzymes, cytochromes, hemoglobin, etc. Thus, the assay procedure discussed herein is useful not only in the assay of what are technically termed peroxidase enzymes, but also in the determination of other materials demonstrating "peroxidative activity."

The reaction which occurs in one of the preferred assay compositions described herein is as follows:

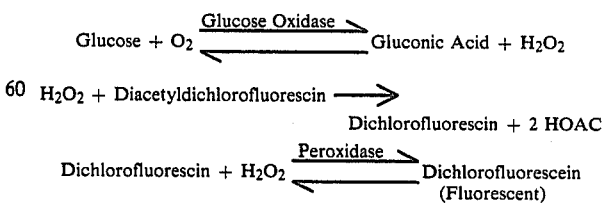

As described hereinabove, the assay compositions of the present invention comprise diacetyldichlorofluorescin and a source of hydrogen peroxide.

Diacetyldichlorofluorescin is readily and commercially available from Eastman Organic Chemicals, Rochester, N.Y.

Any source of hydrogen peroxide can be useful in the successful practice of the instant invention. Of course, hydrogen peroxide itself may be used as the source of the material. This is preferred when the assay reaction is carried out in solution or when the hydrogen peroxide may be added to the reagent system at about the same time as the sample under assay.

In many circumstances, it may, however, be desirable to supply a reagent composition of the type described herein in dry powder form ready for reconstitution with water or to provide the assay composition in the form of a paper or other fibrous or strip material which has been impregnated with reagent which is reconstituted upon application of a liquid assay sample thereto. Yet a further desirable embodiment can be the incorporation of the reagent into one or more layers of a multilayer element of the type described in U.S. Pat. No. 3,992,158.

Under such circumstances a source of hydrogen peroxide which is dry until contacted with water should be used. A preferred class of such sources of hydrogen peroxide are mixtures of an enzyme which demonstrates oxidative activity and substrates for such enzyme. Examples of such mixtures are well known and include by way of example, glucose and glucose oxidase, uric acid and uricase and cholesterol and cholesterol oxidase. Any of these and numerous other similar mixtures of oxidase and substrate when contacted in water and in the presence of oxygen result in decomposition of the substrate with the concomitant production of hydrogen peroxide. Such materials are also considered particularly useful, since they can be freeze-dried or lyophilized to provide dried powder reconstituted with water. Of course, the enzyme and the substrate must be kept separate until the production of the hydrogen peroxide is desired.

Furthermore, since dichlorofluorescin is, as mentioned hereinabove, quite unstable, formation thereof by the reaction of peroxide and diacetyldichlorofluorescin should not be initiated until the peroxidative substance under assay has been added to the assay composition. Other useful hydrogen peroxide sources include chemically bound hydrogen peroxides such as urea peroxide (Robeco Chemicals, Inc.) and the like.

The concentration of the reagents in the assay composition will depend, to a large extent, on the suspected or actual concentration of the material under assay, higher concentrations of reagent being necessary for higher concentrations of material under assay. For concentrations of peroxidative material between about $10^{-5}$ and about $10^{-10}$ M, the following composition has been found particularly useful:

| | |
|---|---|
| diacetyldichlorofluorescin | $10^{-7}$–$10^{-4}$M |
| oxidative enzyme | 1–50 units/ml |
| substrate | 1–100 mg/dl |
| Buffer to maintain pH at | 7–9. |

Useful buffers should be such as not to interfere with the assay reaction. Barbital or phosphate buffers at a concentration of between about 0.01 and 0.1 M have been found useful for this purpose.

When hydrogen peroxide is used as the peroxide source, a concentration of between about $10^{-5}$ and $5 \times 10^{-4}$ M have been found useful in the above-described assay composition.

In a further embodiment of the present invention, the assaying composition comprising diacetyldichlorofluorescin and a source of hydrogen peroxide can be used to determine the amount of peroxidative activity present in a patient's hemoglobin. Thus, a sample of hemoglobin can be added to the assaying composition and the measurement of the fluorescence rate of the resulting dichlorofluorescin will determine the amount of peroxidative activity in the hemoglobin.

The method for detecting peroxidase comprises contacting, in an aqueous medium, the sample under assay with a composition comprising diacetyldichlorofluorescin and a source of hydrogen peroxide and then detecting the resulting dichlorofluorescein. Since the resulting dichlorofluorescein is fluorescent, the detection thereof is easily made by measuring the fluorescence over a short period of time. The amount of peroxidase in the sample is directly related to the rate of fluorescence of the resulting dichlorofluorescin.

The assay composition can be employed in dry chemistry techniques. It can, for example, be incorporated by imbibition impregnation or by coating techniques into a reagent zone of a dry test element, e.g., a reagent layer of a dip-and-read fibrous test strip or a reagent layer of a non-fibrous multilayer element, as described in U.S. Pat. Nos. 3,992,158 of Przybylowicz et al and 4,042,335 of Clement.

Thus, a dry test element for the assay of peroxidase in an aqueous medium, said element having a reagent zone containing an assay composition for peroxidase, is useful when the assaying composition comprises diacetyldichlorofluorescin and a source of hydrogen peroxide.

The element can comprise either layers or zones of reagent and, optionally, spreading agent. Elements containing these zones and/or layers are described in U.S. Pat. Nos. 3,992,158 and 4,069,016 which are herein incorporated by reference.

The substantially dry element can be contacted with a sample for analysis and the resulting dichlorofluorescein can be detected. If the sample itself does not contain an aqueous medium, this could be added with the sample to the dry element.

A particularly preferred test element for the detection of peroxidase in a liquid comprises a spreading layer, a reagent layer and a registration layer, all in fluid contact under conditions of use, and a support, the reagent layer intervening the spreading layer and the registration layer intervening the reagent layer and the support, the reagent layer comprising diacetyldichlorofluorescin and a source of hydrogen peroxide. The registration layer is described in detail in U.S. Pat. No. 4,042,335, columns 11 and 12.

A particularly preferred embodiment of the invention comprises a method for assaying for antigen or antibody present in a sample. This method comprises labeling a known antigen or antibody with peroxidase and carrying out the immunoassay in the conventional manner. Thus, the unknown sample can be added along with the labeled sample to a liquid or web comprising the corresponding antigen or antibody. The labeled and unlabeled antigen or antibody will combine with the corresponding antigen or antibody to form an antigen-antibody precipitate and free labeled antigen or antibody as well as free unlabeled antigen or antibody. The art-recognized determination of the known antigen or antibody is made by measuring the free labeled antigen or antibody.

The measurement of labeled antigen or antibody can be accomplished by assaying for peroxidase by adding the resulting solution to an assaying composition comprising diacetyldichlorfluorescin and a source of hydrogen peroxide and determining the amount of peroxidase by measuring the rate of fluorescence of the resulting dichlorofluorescein.

The following examples will serve to better demonstrate the successful practice of the present invention.

EXAMPLE 1

Fluorescence Assay for Peroxidase

To a 1 $cm^2$ cuvette was added 1.4 ml phosphate buffer solution (PBS) containing 0.01 M sodium phosphate, 0.1 N NaCl, pH 7.5, 0.200 ml diacetyldichlorofluorescin ($1 \times 10^{-5}$ M in PBS) and 200 $\mu l$ hydrogen peroxide ($1 \times 10^{-3}$ M in water). Reaction was initiated by the addition of peroxidase (horseradish) of the indicated concentration. The rate was measured in a Farrand Mk I fluorometer with excitation monochrometer at 490 nm and emission monochrometer at 520 nm. The rate was linear for 5 minutes. In FIG. 1, the rates of fluorescence increase per minute are plotted as a function of peroxidase concentration.

Peroxidase concentrations of up to $1.32 \times 10^{-5}$ M were measurable when the hydrogen peroxide concentration was increased fifty fold and the dichlorofluorescin concentration increased twofold.

EXAMPLE 2

Multilayered Element for the Fluorometric Determination of Peroxidase

A multilayered element was prepared according to the following:

A lexan support was coated with a reagent layer comprised of deionized gelatin (Type V) (4.5 $g/m^2$), 5,5-dimethyl-1,3-cyclohexanedione (0.4 $g/m^2$), glucose oxidase (538 Units/$m^2$), bis(vinyl sulfonyl methyl)ether (0.05 $g/m^2$), surfactant (10-G) (0.01 $g/m^2$), zinc acetate (0.01 $g/m^2$), dichlorofluorescin diacetate (0.01 $g/m^2$) in 0.02 M phosphate buffer at pH 8.0; an enzyme layer comprising deionized gelatin (2.9 $g/m^2$), colloidal silver (1.02 $g/m^2$), catalase (86,000 U/$m^2$), bis(vinyl sulfonyl methyl)ether (0.04 $g/m^2$), surfactant (10-G) (0.007 $g/m^2$); a subbing layer comprised of poly-N-isopropylacrylamide (0.4 $g/m^2$); and a spreading layer comprised of $TiO_2$(70.0 $g/m^2$), cellulose acetate (10.0 $g/m^2$), glucose (0.5 $g/m^2$), and polyacrylamide particles (L60 mesh) (0.01 $g/m^2$).

The element was tested by spotting on 10 $\mu l$ of solution containing dinitrophenyl peroxidase conjugate* and measuring the rate at which the fluorescent signal increased, when excited at 460 nm and emitted at 520 nm, as in Example 1. Results are shown in Table I.
*Prepared by coupling dinitrobenzene sulfonic acid to peroxidase obtained from horseradish

TABLE I

| Conc. DNP . POD (M) | Relative Rate |
| --- | --- |
| $5.0 \times 10^{-6}$ | 7.5 |
| $2.5 \times 10^{-6}$ | 4.8 |
| $1.25 \times 10^{-6}$ | 1.92 |
| $6.25 \times 10^{-7}$ | 0.79 |
| $3.13 \times 10^{-7}$ | 0.27 |
| $1.57 \times 10^{-7}$ | 0.09 |
| $7.85 \times 10^{-8}$ | 0.05 |

TABLE I-continued

| Conc. DNP . POD (M) | Relative Rate |
| --- | --- |
| $3.93 \times 10^{-8}$ | 0.028 |
| 0 | 0 |

The invention has been described in detail with particular reference to preferred embodiments thereof, but it will be understood that variations and modifications can be effected within the spirit and scope of the invention.

I claim:

1. A composition useful for the determination of a substance having peroxidative activity, said composition, consisting essentially of diacetyldichlorofluorescin and a source of hydrogen peroxide in a concentration of from about $10^{-6}$ to $10^{-2}$ M, the ratio of diacetyldichlorofluorescin to hydrogen peroxide or generated hydrogen peroxide ranging from 1:5 to 1:100.

2. The composition of claim 1 wherein said source of hydrogen peroxide comprises an enzyme and an enzyme substrate which, when contacted in an aqueous medium in the presence of oxygen, release hydrogen peroxide.

3. The composition of claim 1 wherein said source of hydrogen peroxide is hydrogen peroxide.

4. The composition of claim 1 wherein said source of hydrogen peroxide is urea peroxide.

5. The composition of claim 2 wherein said enzyme is an oxidative enzyme and said substrate is the corresponding substrate for said oxidative enzyme.

6. The composition of claim 2 wherein said enzyme is glucose oxidase and said substrate is glucose.

7. The composition of claim 2 wherein said enzyme is uricase and said substrate is uric acid.

8. The composition of claim 2 wherein said enzyme is cholesterol oxidase and said substrate is cholesterol.

9. The composition of claim 1 further including a buffer which maintains the pH of the composition at a pH of between about 7 and 9.

10. The composition of claim 1 wherein the concentration of diacetyldichlorofluorescin is from about $10^{-7}$ to $10^{-3}$ M.

11. A method for assaying peroxidase comprising the steps of
  (a) contacting in an aqueous medium a sample for analysis and a composition consisting essentially of diacetyldichlorofluorescin and a source of hydrogen peroxide in a concentration from about $10^{-6}$ to $10^{-2}$ M to produce dichlorofluorescein, the ratio of diacetyldichlorofluorescin to hydrogen peroxide or generated hydrogen peroxide ranging from 1:5 to 1:100; and
  (b) detecting the dichlorofluorescein.

12. The method of claim 11 wherein the dichlorofluorescein is detected by fluorescence rate measurements.

13. The method of claim 11 wherein said source of hydrogen peroxide comprises an enzyme and an enzyme substrate which, when contacted in an aqueous medium in the presence of oxygen, release hydrogen peroxide.

14. The method of claim 11 wherein said source of hydrogen peroxide is hydrogen peroxide.

15. The method of claim 11 wherein said source of hydrogen peroxide is urea peroxide.

16. The method of claim 13 wherein said enzyme is an oxidative enzyme and said substrate is the corresponding substrate for said oxidative enzyme.

17. The method of claim 11 wherein the concentration of diacetyldichlorofluorescin in said composition is from about $10^{-7}$ to about $10^{-3}$ M.

18. The method of claim 11 wherein said composition further includes a buffer which maintains the pH of the composition at a pH of between about 7 and 9.

19. A method for assaying peroxidase comprising the steps of
(a) contacting a substantially dry element comprising a reagent having a composition consisting essentially of diacetyldichlorofluorescin and a dry source of hydrogen peroxide at a concentration of from about $10^{-6}$ to $10^{-2}$ M with a sample for analysis, the ratio of diacetyldichlorofluorescin to generated hydrogen peroxide ranging from 1:5 to 1:100; and
(b) detecting the dichlorofluorescein resulting from said contact.

20. The method of claim 19 wherein the dichlorofluorescein is detected by fluorescence rate measurements.

21. The method of claim 19 wherein said source of hydrogen peroxide comprises an enzyme and an enzyme substrate which, when contacted in an aqueous medium in the presence of oxygen, release hydrogen peroxide.

22. The method of claim 19 wherein said source of hydrogen peroxide is urea peroxide.

23. A dry test element for the assay of peroxidase in an aqueous liquid, said element having a reagent zone containing an assay composition for peroxidase, said assay composition consisting essentially of diacetyldichlorofluorescin and a dry source of hydrogen peroxide at a concentration of from about $10^{-6}$ to $10^{-2}$ M, the ratio of diacetyldichlorofluorescin to generated hydrogen peroxide ranging from 1:5 to 1:100.

24. The element of claim 23 wherein said source of hydrogen peroxide comprises an enzyme and an enzyme substrate which, when contacted in an aqueous medium in the presence of oxygen, release hydrogen peroxide.

25. The element of claim 23 wherein said source of hydrogen peroxide is urea peroxide.

26. The element of claim 23 wherein said enzyme is an oxidative enzyme and said substrate is the corresponding substrate for said oxidative enzyme.

27. An element for the detection of peroxidase comprising fibrous material which is impregnated with a reagent consisting essentially of diacetyldichlorofluorescin and a source of hydrogen peroxide at a concentration of from about $10^{-6}$ to $10^{-2}$ M, the ratio of diacetyldichlorofluorescin to hydrogen peroxide or generated hydrogen peroxide ranging from 1:5 to 1:100.

28. The element of claim 27 wherein said fibrous material is paper.

29. The element of claim 27 wherein said source of hydrogen peroxide is hydrogen peroxide.

30. The element of claim 27 wherein said source of hydrogen peroxide is urea peroxide.

31. The element of claim 27 wherein said source of hydrogen peroxide comprises an enzyme and an enzyme substrate which, when contacted in an aqueous medium in the presence of oxygen, release hydrogen peroxide.

32. An element for the detection of peroxidase comprising a spreading layer and a reagent layer in fluid contact under conditions of use, said reagent layer comprising a reagent consisting essentially of diacetyldichlorofluorescin and a dry source of hydrogen peroxide at a concentration of from about $10^{-6}$ to $10^{-2}$ M, the ratio of diacetyldichlorofluorescin to generated hydrogen peroxide ranging from 1:5 to 1:100.

33. The element of claim 32 wherein said source of hydrogen peroxide comprises an enzyme and an enzyme substrate which, when contacted in an aqueous medium in the presence of oxygen, release hydrogen peroxide.

34. The element of claim 32 wherein said source of hydrogen peroxide is urea peroxide.

35. The element of claim 33 wherein said enzyme is an oxidative enzyme and said substrate is the corresponding substrate for said oxidative enzyme.

36. An element for the detection of peroxidase in a liquid, the element comprising a spreading layer, a reagent layer and a registration layer all in fluid contact under conditions of use and a support, the reagent layer intervening the spreading layer and the registration layer intervening the reagent layer and the support, the reagent layer comprising a reagent consisting essentially of diacetyldichlorofluorescin and a dry source of hydrogen peroxide at a concentration of from about $10^{-6}$ to $10^{-2}$ M, the ratio of diacetyldichlorofluorescin to generated hydrogen peroxide ranging from 1:5 to 1:100.

37. The element of claim 36 wherein said source of hydrogen peroxide comprises an enzyme and an enzyme substrate which, when contacted in an aqueous medium in the presence of oxygen, release hydrogen peroxide.

38. The element of claim 36 wherein said source of hydrogen peroxide is urea peroxide.

39. The element of claim 37 wherein said enzyme is an oxidative enzyme and said substrate is the corresponding substrate for said oxidative enzyme.

40. The element of claim 36 wherein said reagent layer further comprises a buffer which maintains the pH of the reagent at a pH of between about 7 and 9.

41. A method of assaying for antigen or antibody present in a sample to be tested comprising:
(a) labeling a known amount of antigen or antibody with peroxidase and adding said labeled antigen or antibody with said sample to be tested to a known amount of corresponding antigen or antibody; and
(b) determining the amount of unknown antigen or antibody by
(i) contacting in an aqueous medium the mixture of (a) and a composition consisting essentially of diacetyldichlorofluorescin and a source of hydrogen peroxide at a concentration of from about $10^{-6}$ to $10^{-2}$ M to produce dichlorofluorescein, the ratio of diacetyldichlorofluorescin to hydrogen peroxide or generated hydrogen peroxide ranging from 1:5 to 1:00;
(ii) detecting the dichlorofluorescein.

* * * * *